United States Patent [19]

Commons et al.

[11] 4,093,625

[45] June 6, 1978

[54] 6-SULFUR ANALOGS OF PENICILLINS AND CEPHALOSPORINS

[75] Inventors: Thomas J. Commons, Boston; John C. Sheehan, Lexington; Young-Sek Lo, Brookline, all of Mass.

[73] Assignee: Massachusetts Institute of Technology, Cambridge, Mass.

[21] Appl. No.: 712,540

[22] Filed: Aug. 9, 1976

[51] Int. Cl.$^2$ .................. C07D 499/00; C07D 501/00; C07D 501/04; C07D 501/10
[52] U.S. Cl. .................. 260/306.7 C; 204/158 R; 260/239.1; 424/246; 424/270; 424/271; 544/18; 544/22; 544/26; 544/28; 544/29
[58] Field of Search ...................... 260/306.7 C, 239.1

[56] References Cited

PUBLICATIONS

Slusarchyk et al., J. Org. Chem., vol. 38, pp. 943–949, (1973).
Jen et al., J. Org. Chem., vol. 38, pp. 2857–2859, (1973).

*Primary Examiner*—Gerald A. Schwartz
*Attorney, Agent, or Firm*—Arthur A. Smith, Jr.; David G. Conlin

[57] ABSTRACT

Sulfur analogs of 6-aminopenicillanic acid and biologically active derivatives thereof are formed in a photochemical reaction of the esters of 6-diazopenicillanic acid with thiol compounds. Sulfur analogs of 7-aminocephalosporanic acid and biologically active derivatives thereof may be analogously formed in a photochemical reaction of the esters of 7-diazocephalosporanic acid with thiol compounds, or preferably, are formed from the corresponding sulfur analogs of 6-aminopenicillanic acid and derivatives thereof, through sulfoxide rearrangement of the thiazolidine ring of penicillins to the dihydrothiazine ring system of cephalosporins. These sulfur analogs of penicillins and cephalosporins are new antibacterial agents and display antibacterial activity against a wide variety of organisms.

18 Claims, No Drawings

6-SULFUR ANALOGS OF PENICILLINS AND CEPHALOSPORINS

BACKGROUND OF THE INVENTION

This invention relates to derivatives of penicillins and cephalosporins, and more particularly to sulfur analogs of 6-aminopenicillanic acid and 7-aminocephalosporinic acid and biologically active derivatives thereof.

In U.S. Pat. No. 3,159,617, there is taught the first commercial synthesis of 6$\beta$-aminopenicillanic acid and penicillin derivatives based thereon. A vast number of derivatives of the 6$\beta$-aminopenicillanic acid may be formed by introduction of various groups into the amino group of the acid. Thus, acyl groups, isocyanates, isothiocyanates, halogen compounds, methylisoureas, ethylene oxide, ethylene imine, and the like have been introduced into the amino group of the 6$\beta$-aminopenicillanic acid to form both biologically active and biologically inactive derivatives.

Many of the derivatives of 6$\beta$-aminopenicillanic acid, especially those derivatives formed by acylation, have become useful drugs. For example, ampicillin and carbenicillin have broadened the spectra of activity to include use against certain Gram-negative organisms while methicillin shows good activity against certain resistant staphylococci.

In an effort to find new biologically active derivatives of 6$\beta$-aminopenicillanic acid, attempts have been made to modify the parent compounds by myriad methods, in addition to the mere functionalization of the amino group. Thus, stimulated by the elucidation of the structure of the cephalosporins, there have been attempted modifications of the thiazolidine moiety of 6$\beta$-aminopenicillanic acid. This transformation is particularly useful since cephalosporins are not readily available from nature. Thus, much effort has been concentrated on the investigation of possible transformations of the thiazolidine ring to the dihydrothiazine ring without any concomitant change of the chemically sensitive $\beta$-lactam moiety. These efforts are described by D. H. R. Barton and T. G. Sammes, Proc. R. Soc. Lond. B, 179 345 (1971).

Other attempts have been made to modify 6$\beta$-aminopenicillanic acid through reaction of the $\beta$-lactam moiety, but such attempts are relatively few and are focused on variation of the substituents of sterochemistry of the C-6 carbon in the penam system. Primarily, four types of modifying reactions are reported, namely acylation, epimerization, alkylation and diazotization.

One successful example of the epimerization reaction is reported by G. E. Gutowski, Tet.Lett., (1970), 1779 and 1863. However, this penicillin having the epimerized C-6 substituent is devoid of any biological activity. With regard to alkylation at the C-6 position, most attempts, based upon earlier predictions that the introduction of an $\alpha$-methyl group at the C-6 position might enhance antibiotic activity, have been directed to such introduction. Further, both direct and indirect $\alpha$-hydroxylalkylation of the penicillin nucleus at C-6 with benzaldehyde an formaldehyde has been reported by R. Riner and P. Zeller, Helv., Chim., Acta 51, 1905 (1968). These derivatives and other $\alpha$-alkylated derivatives show some biological activity, but both display substantially less activity than the well known penicillin G.

Deamination of 6$\beta$-aminopenicillanic acid by sodium nitrite in mineral acid proceeds with inversion at C-6, resulting in the C-5 and C-6 protons being trans-oriented in the product. Moreover, when the reaction is run in the presence of a haloacid, a 6$\alpha$-halo product is obtained. Deamination of 6$\beta$-aminopenicillanic acid by sodium nitrite with oxy acids is reported by T. Hauser and H. P. Sigg, Helv. Chim. Acta, 50, 1327 (1967). With such oxy acids, 6$\alpha$hydroxypenicillanic acid is isolated as the benzyl ester. Ready transformation produces the $\alpha$-oxygen analog, of penicillin V, 6 $\alpha$-phenoxyacetoxypenicillanic acid. This material also exhibits no biological activity.

Similar chemical transformations and derivatizations in the cephalosporin antibiotic series are reported in part by R. B. Morin and B. G. Jackson, "Chemistry of Cephalosporin Antibiotics, " Progress in the Chemistry of Organic Natural Products XXVIII, Wein, Springer-Verlag (1970).

Further, two new series of these penicillins and cephalosporins have recently been described in copending U.S. patent applications Ser. Nos. 347,772, filed Apr. 3, 1973, 494,507, filed Aug. 5, 1974, and 616,979, filed Sept. 26, 1975. These series, the carbon and oxygen analogs of penicillins and cephalosporins, are characterized by the replacement of the 6$\beta$-nitrogen of the "normal" antibiotic with carbon or oxygen respectively. These novel analogs and the wide variety of derivatives obtainable therefrom are biologically active and provide new series of antibiotics.

For brevity, the commonly accepted abbreviations of 6-APA for 6$\beta$-aminopenicillin acid, 6-OPA and 6-CPA for the oxygen and carbon analogs thereof, 7-ACA for 7$\beta$-aminocephalosporanic acid and 7-OCA and 7-CCA for the oxygen and carbon analogs thereof will be used throughout the specification.

SUMMARY OF THE INVENTION

The present invention provides a synthetic route to, and displays the antibiotic utility of, a novel penicillin and cephalosporin genus, the sulfur analogs of 6-aminopenicillanic acid (6-APA) and 7-aminocephalosporanic acid (7-ACA) and biologically active derivatives thereof. The materials may be produced by a photochemical reaction of esters of 6-diazopenicillanic acid or 7-diazocephalosporanic acid and reactants funtionalized by a thiol substituent. Such reaction results in the novel series of antibiotic compounds whose further derivatization by reactions similar to those familiar in the penicillin and cephalosporin art provides large numbers of biologically active sulfur-penicillins and cephalosporins respectively. Moreover, the sulfur-penicillin compounds may be transformed through sulfoxide rearrangement of the thiazolidine ring to the biologically active corresponding sulfur analogs of 7$\beta$-aminocephalosporins (7-ACA) and biologically active derivatives thereof. Therefore, this invention encompasses synthetic schemes to, and the biological useful activity of, 6$\beta$-aminopenicillins and 7$\beta$-aminocephalosporins wherein the side chain nitrogen atom has been replaced by a sulfur atom, and various derivatives thereof.

DESCRIPTION OF THE PREFERRED EMBODIMENT

The employment of esters of 6-diazopenicillanic and 7-diazocephalosporanic acid as sources of novel antibacterial agents, particularly the carbon and oxygen analogs of 6-APA and 7-ACA, 6-CPA/6-OPA and 7CCA/7-OCA, respectively, has been described in copending U.S. patent application Ser. Nos. 347,772, 494,507 and 616,969, described above and incorporated herein by reference.

It has now been found that esters of 6-diazopenicillanic and 7-diazocephalosporanic acid can provide the penicillin and cephalosporin reactants whose photochemical transformation in the presence of an acidic thiol-substituted reactant effects the replacement of the nitrogen atom in the respective 6 and 7 side chain with a sulfur atom. These resultant sulfur analogs of 6-APA and 7-ACA and their derivatives display biological activity against a wide variety of organisms. Further, many of the compounds prepared in accordance with the invention, e.g. 6-SPA or 7-SCA, can be used as intermediates to produce highly biologically active compounds. The penicillanic sulfur analogs themselves, for example, can serve as the primary reactant for sulfoxide rearrangement of the thiazolidone ring to corresponding biologically active sulfur analogs of 7-ACA and derivatives thereof.

The synthetic approach to these two antibiotic series, characterized by a sulfur atom at the 6β and 7β positions involves first the synthesis of the appropriate esters, 6-diazopenicillanate and 7-diazocephalosporanate, respectively. Such a synthetic scheme is described in J. C. Sheehand, Y. S. Lo, J. Loliger and C. C. Podewell, J. Org. Chem., 39:1444 (1974), and involves the diazotization of the corresponding penicillin or cephalosporin with dinitrogen tetroxide and treatment of the resultant nitroso derivative with silica gel or a base in a refluxing organic solvent.

The photochemical transformation of the diazopenicillanate or cephalosporanate to the corresponding sulfur-penicillin or cephalosporin is effected by the irradiation of a solution of this reactant with a thiol containing compound. Esters useful in such reactions include those having the following general formulas:

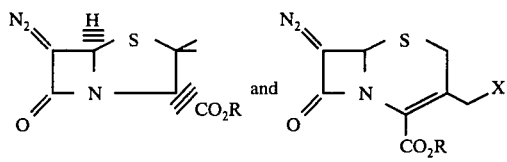

wherein R is a well known protective group for acids, such as (1) substituted or unsubstituted aliphatic, alicyclic or aromatic, e.g. alkyl (preferbly lower alkyl such as methyl, ethyl, propyl, t-butyl, βββ-trichloroethyl, etc.), cycloalkyl (e.g. cyclohexyl), aryl (e.g. phenyl, tolyl), aralkyl (e.g. benzyl, methylbenzyl, p-nitrobenzyl, 9-anthrylmethyl, etc.) or alkaryl; (2) substituted or unsubstituted phenacyl, e.g. phenacyl, p-methoxy phenacyl, m-chlorophenacyl; (3) salts including alkali metal salts such as sodium or potassium salts, as well as quaternary ammonium groups such as N-ethyl piperidono and dicyclohexylamino; or (4) organo silyl groups, e.g. alkyl silyls such as trimethyl silyl, triethyl silyl, etc., and, with regard to the diazocephalosporin, X is hydrogen or an organic nucleophile, e.g. halogen, hydroxyl, alkoxyl, aryloxyl, alkylamino, arylamino, including tertiary amino, such as pyridinyl (see U.S. Pat. No. 3,218,318, issued Nov. 16, 1965, to E. H. Flynn, incorporated herein by reference) acyloxy, carboxyl, carbonyl, sulfonyl, carbamyl, thio-carboxyl, and analogous functionalities. Suitable protective groups (R) are well knownm and are described, for example, in J. F. W. McOmie, Protective Groups In Organic Chemistry, (Plenum Press 1973), particularly in chapter 7, p. 183 et seq., "Protection of Carboxyl Groups, " by E. Haslam, incorporated herein by reference. Preferably the protective group used can be removed in acidic medium, and do not render the compound substantially photoreactive (except for the diazo linkage) above a wave length of about 280 mm. Most preferred at present are lower alkyl, particularly t-butyl, halogenated lower alkyl, particularly βββ-trichloroethyl, phenacyl and trimethylsilyl.

X is preferably hydrogen or acyloxy, e.g. formyloxy, acetoxy, phenylacetoxy benzoyloxy, but a wide variety of substituents can be placed there. See E. H. Flynn, Cephalosporins and Penicillins, 134–180 (Academic Press, 1972) incorporated herein by reference.

The above 6-diazopenicillanate or 7-diazocephalosporanate esters are reacted under irradiation with a thiol of the general formula R¹SH to give compounds of the formulas:

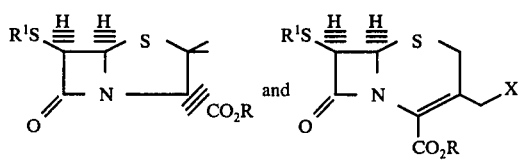

R¹ in each case represents an organic moiety which is electrophillic as compared to the sulfur to which it is attached. A wide variety of substitutents are suitable, including substituted or unsubstituted aliphatic, e.g. alkyl, preferably lower alkyl, such as methyl, ethyl, propyl, hexyl, etc.; alicyclic, e.g. cycloalkyl, such as cyclopentyl, cyclohexyl, methylcyclohexyl; aromatic, e.g. phenyl, benzyl, tolyl; acyl, e.g. benzoyl, phenoxyacetyl, chloroacetyl and bromoacetyl; carboxylic carbonic; sulfonic; and amide radicals.

While a wide variety of R¹ group substitutions are useful in this invention, it is believed that the photochemical reaction is aided, e.g. effected at a faster rate, when the R¹ group tends to enhance the acidity of the thiolic proton, and thus such R¹ groups are referred. Most preferred are those R¹ groups which are bound to the sulfur by a carbonyl group. Suitable R¹ substituents include hydrogen, formyl, acetyl, phenyl, phenylacetyl, phenoxyacetyl, p-aminophenylacetyl, α-carboxylphenylacetyl, benzyl, benzoyl, 2-thienylacetyl, aminocarbamyl, phenylglycyl, methyl sulfonyl, benzyl sulfonyl, o-aminophenylsulfonyl, p-aminobenzylsulfonyl, carbobenzoxy, α-carbonaphthoxy, carbo82-thienylmethoxy), and (1-phenyl 2-formylamino)ethoxycarbonyl.

The irradiation is preferbly accomplished in an inert atmosphere, e.g. under a mercury lamp equipped with a pyrex filter in the presence of an excess of the thiol substituted compound. Suitable lamps, such as the Hanovia 450 watt medium pressure mercury lamp, are well known in the art.

A wide variety of solvents which are well known in the photochemical art may be effectively employed in this transformation. Basically any solvent is suitable if the reactants and products are soluble in it and it does not substantially interfere with the reaction, e.g. by absorbing in the wave length range at which the reaction is conducted, or by acting as a free radical trap. Suitable solvents include substituted and unsubstituted alkyls, alcohols, alkaryls and aralkyls, and others well known in its art. Most preferred at present are halogenated lower alkyls, such as carbon tetrachloride, methylene chloride, trichloro ethane, fluorotrichloromethane, etc. Most preferred is carbon tetrachloride.

Removal of the acid protective group, R, from the above compounds produces the free acids, 6-SPA and 7-SCA:

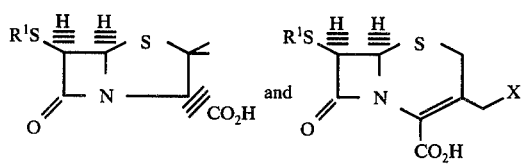

While it should be understood that some of the aforesaid acid protective groups may be more difficult to remove than others, these groups have heretofore been used as protective groups in analogous penicillins and cephalosporins and the carbon and oxygen analogs thereof. Removal of such groups is effected in accordance with well-recognized procedures, dependent upon the identity of the group. See McOmie, Protective Groups In Organic Chemistry, supra.

These free acids, exhibiting a reactivity similar to 6-APA, 6-SPA, 6-OPA, 7-CCA and 7-OCA, may be esterified to sulfur penicillanates and cephalosporanates of the general formulas:

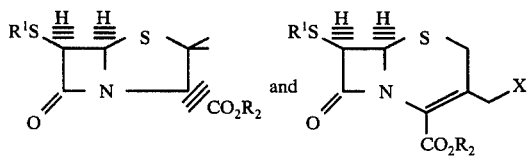

where $F^1$ and X are as above described, and $R^2$ represents pharmaceutically acceptable groups, as well known in the art. $R^2$ may be selected from any of the groups from which R may be selected, as described above, namely, either R or $R^2$ may be hydrogen or substituted or unsubstituted (1) aliphatic, alicyclic or aromatic, e.g. alkyl, preferably lower alkyl such as methyl, ethyl or propyl, alkenyl, preferably lower alkenyl, such as ethenyl, propenyl and butenyl, alkinyl, preferably lower alkinyl such as ethinyl, propinyl and butinyl; cycloalkyl or cycloalkenyl, such as cyclohexyl; aralkyl such as benzyl and phenylethyl; (2) acyl compounds, including acylalkyl, preferably lower acylalkyl such as acetylmethyl, acetylethyl, and acetylpropyl; acylamino, preferably lower acylamino, such as acetylamino, propionylamino, and butyrlamino; acylaminoalkyl, preferably lower acylaminoalkyl, such as acetylaminoethyl, acetylaminoethyl, imino (see U.S. Pat. No. 3,876,630, issued Apr. 8, 1975 to Ishimara et al), and arylacyls such as the phenylacyl and its derivatives previously mentioned in connection with R; (3) salt formers, e.g. alkali metal ions, or organic ammonium groups such as tri(alkyl)ammonium (preferably tri(lower allyl) ammonium, e.g. triethylammonium) or piperidino or N-alkyl (preferably lower alkyl)-piperidino, or benzylammonium; and (4) organo silyl groups, preferably tri(lower alkyl)silyls.

$R^1$ may be appropriately selected so as to adduce facile cleavage of the $R^1$-S bond, such cleavage results in the parent series of sulfur analogs having the following general formulas:

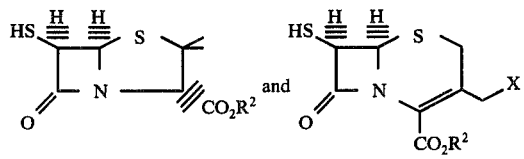

wherein $R^1$ and X are as above described. Substituents useful in such cleavage reaction are characterized by $R^1$ being a good leaving group, e.g. good electron withdrawing groups. These include chloroacetyl, bromoacetyl, ethoxyacetyl, nitrogenzoyl, dimethoxylmethyl, and substituted and unsubstituted phenoxyacetyl.

These thiol compounds, of course, on removal of the pharmaceuticaly acceptable group $R^2$ as discussed above with respect to R, afford the parent compounds 6-SPA and 7-SCA respectively:

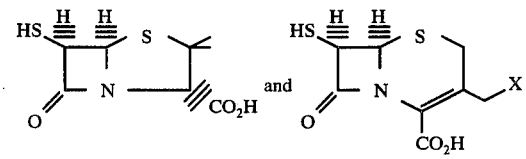

where X is as before described.

This parent moiety is readily functionalized at the 6β or 7α position, and/or esterified on the acid substitutent to produce sulfur analogs of the general formula as follows:

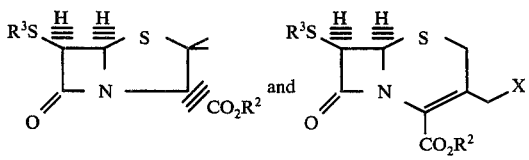

wherein $R^2$ is as above described and $R^3$ an organic electrophile similar to those well known in penicillin and cephalosporin side chain technology. Preferably, $R^3$ is selected from the same substituents give above for $R^1$. Thus after introduction of sulfur at the 6 position in the penicillanic compounds, both the substituent $R_1$ (or $R^3$) attached to the sulfur, and the substituent R (or $R^2$) on the 3-carboxylic acid ester can be changed by reactions of which the skilled in the art will be well aware. With the regard to the cephalosporanic compounds, the corresponding (or $R^2$) and $R^1$ (or $R^3$) can similarly be varied, and the X substituant can also be varied through reactions well known in the analogous modification of the esters 7ACA, 7CCA and 7OCA.

For illustrative purposes only the varied penicillanic interconversions described above are depicted in the following scheme where R is βββ-trichloroethyl, $R^1$ is phenoxyacetyl, $R^2$ is benzyl, and $R^3$ is carbomethoxy:

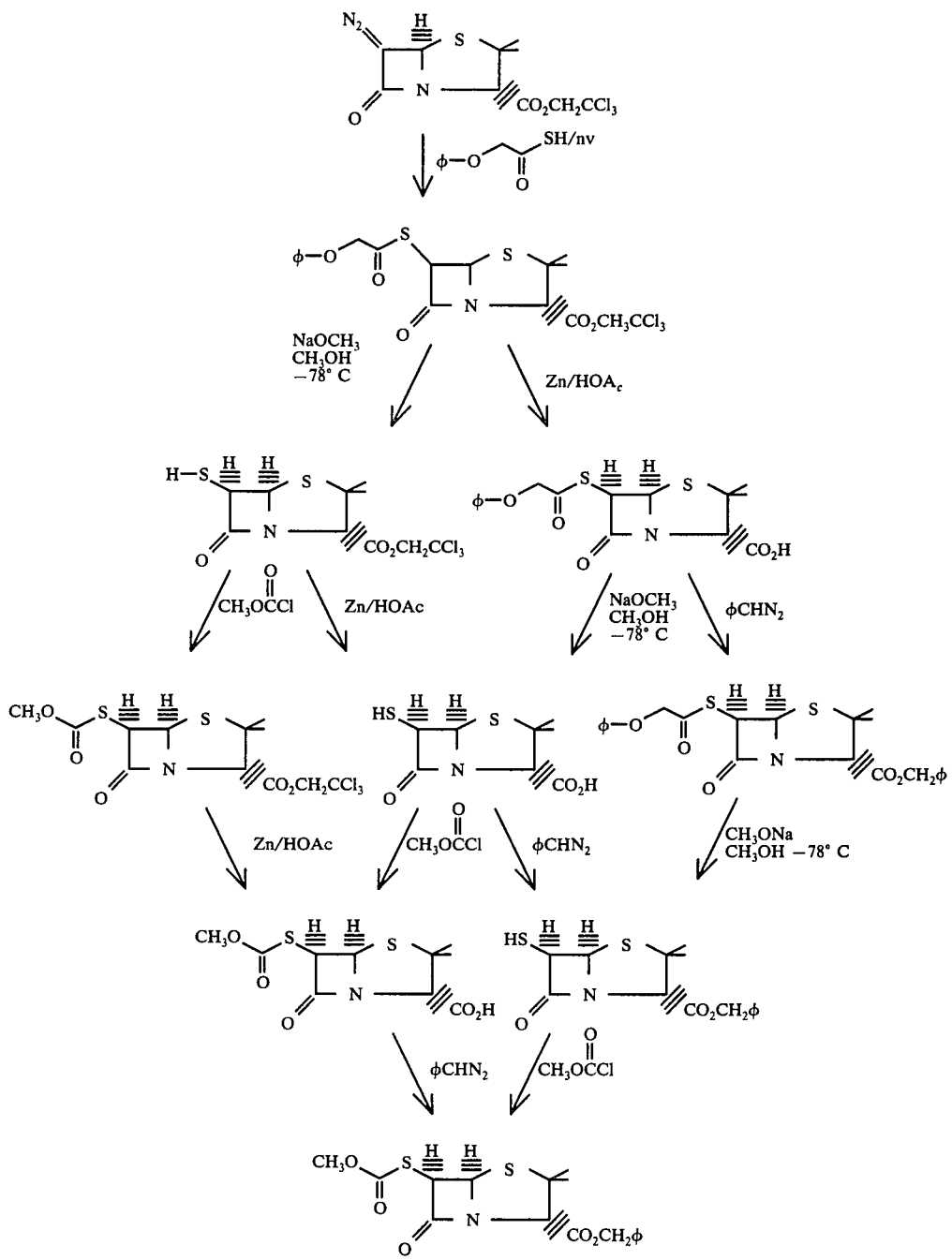
A similar reaction scheme for the cephalosporin series wherein R is t-butyl; $R^1$ is phenoxyacetyl; $R^2$ is trimethylsilyl; $R^3$ is phenylsulfonyl and x is acetoxy, would be as follows:
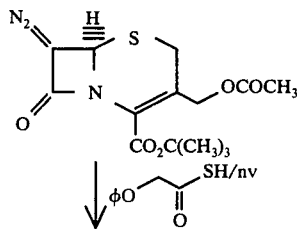

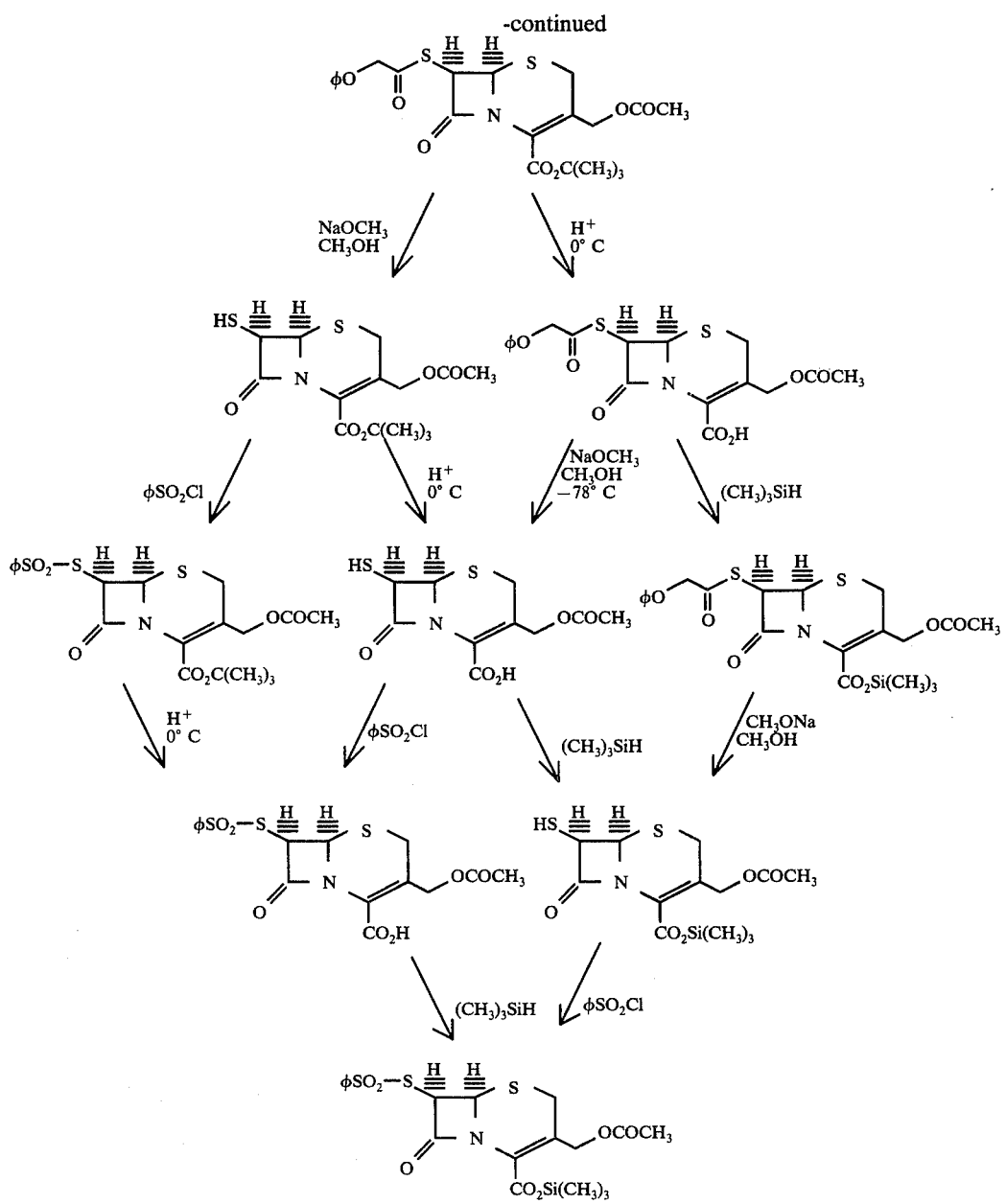

In addition to the above-noted varied interconversions of 6β-thiol penicillins, the esters of this novel genus are amenable to sulfoxide thiazolidine ring rearrangement to the corresponding 7β-thiol cephalosporanates and biologically active derivatives thereof. The rearrangement scheme involves the oxidation of the sulfur analogs of 6-APA and the rearrangement of the resulting sulfoxide to the respective sulfur analogs of 7ACA. Similar schemes for preparation of non-thiol cephalosporins from non-thiol penicillins are known. See, e.g., Morin et al, "Chemistry of Cephalosporin Antibiotics XV," J. Amer. Chem. Soc. 91: 1401 (1969).

The initial sulfur oxidation can be accomplished by varied techniques well known in the art. Numerous suitable oxidizing agents for forming the sulfoxide are known, such as m-chloroperbenzoic acid, ozone, sodium metaperiodate, hydrogen peroxide, and alkyl hydroperoxides, preferably lower alkyl hydroperoxides, e.g. methyl, ethyl, propyl or butyl hydroperoxide, are representative among numerous such reagents. See Fiezer, Reagents for Organic Synthesis (J. Wile & Sons, 1967). The oxidative schemeis preferably carried out in an organic solvent, in which the reactants are soluble, but which do not take part in or interfere with the reaction. Particularly preferred solvents include halogenated alkanes, preferably lower alkanes such as chloroform or methylene chloride. For example, a solution of oxidizing agent such as m-chloroperbenzoic acid in methylene chloride may be added dropwise to a solution of the 6β-thiol pencillinate at 0° C and the oxidation allowed to proceed to completion.

The resultant sulfoxide of an ester of a sulfur analog of 6-APA may be transormed by rearrangement into the corresponding ester of sulfur analog of 7-ACA. This rearrangement is preferably carried out by heating the sulfoxide with a trace of acid or acid-producing reactants. Reactants useful for this purpose include, for example, derivatives of sulfonic acid such as alkylsulfonic acid or arylsulfonic acid, e.g. methanesulfonic acid or p-toluenesulfonic acid, and organic carboxylic acids or anhydrides such as formic, acetic, propionid, phenylacetic or benzoic acid or acetic or benzoic anhydride. The acid need only be present in catalytic amounts. Theoretically one molecule would be sufficient since the acid is regenerated on completion of the reaction. On the other hand, the acid should not be present in such large amounts as to attack the β-lactam ring. Preferably the acid is present in an amount of about 0.005 to 0.2 moles per molle of the sulfoxide, more preferbly about 0.01 to 0.1 moles per mole sulfoxide.

Such heating is preferably carried out in 80-100° C in solvents wherein the water produced as a by-product to the transformation can be azeotropically distilled from the reaction mixture to aid in effecting complete conversion and to avoid attack on the double bond. Suitable solvents sre those which produce an azeotropic mixture with water, having suitable boiling points, but do not adversely affect the reaction, and include without limitation acetic anhydride, benzene, xylene, N,N-dimethylacetamide (DMAc), toluene, and others known in the art.

Illustrative of this reactive sequence is the following scheme, where $R^1$ and $R^2$ are as above described:

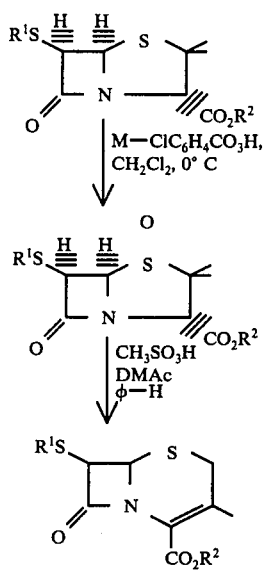

The desired transformation having been effected, the sulfur analog of 7-ACA, of the following general formula:

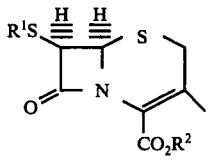

where $R^1$ and $R^2$ are as described before, may be readily modified buy those functionalization and side chain reaction schemes well known in the cephalosporin art under conditions similar to those utilized in the derivation of the esters of 7-ACA, 7-OCA, and 7-CCA to afford myriad compounds of the following formula:

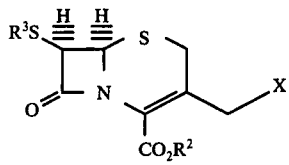

wherein $R^3$, $R^2$ and X are hydrogen or as above described.

The antibiotic compounds of the present invention may be administered to mammals in essentially the same ways the previously known penicillin- and cephalosporin-based antibiotics are administered. They can be administered to mammals, e.g. humans, dogs, mice, rats, etc., orally, parenterally, rectally, or typpically (e.g. for treatment of skin infections). Common dosages for oral administration, for example, range from about 1 to 200 mg/kg/day, in divided dosages. The compounds can be administered as such or in the form of pharmacologically acceptable salts, and may be admixed with carriers or adjuvants or both. In such preparations the ratio of the therapeutic substance and the carriers and adjuvants may vary from about 1% to 99%.

The preparations may either be produced as for instance, tablets, pills or supositories, or can be supplied in medical containers, such as capsules, or as regards mixtures they can be filled in bottles. Pharmaceutically acceptable, organic or inorganic, solid or liquid carriers may be used, suitably for oral or parenteral administration or for topical application, in manufacturing the preparations. Gelatine, lactose, starch, magnesium stearate, micronized silica gel, cocoa butter, talc, vegetabilic and animalic fats and oils, vegetabilic rubber and polyalkylene glycol an other known carriers for pharmaceuticals are all suitable for manufacturing preparations of said compounds. Preparations for parenteral use include an ampoule of a sterile solution or suspension with water or other pharmaceutically acceptable liquid as the carrier therefor, or an ampoule of sterile powder for dilution with a pharmaceutically acceptable liquid. The preferred salt of the esters is the hydrochloride, but salts with other inorganic or organic acids, also antibiotically active acids, may be used, for instance phosphates, acetates or salts witjh phenoxymethylpenicillin. Moreover the preparation may contain other pharmaceutical active components, being suitably administratable together with said esters when treating infectious diseases, e.g. other suitable antibiotical substances, as well as one or more of ingredients such as diluents, buffers, flavoring agents, binders, surface active agents, thickeners, lubricants, preservations, etc.

An exemplary formulation suitable for tabletting would contain about 75% by weight of 6β-(phenylcarbothio)penicillanic acid or 7β-(phenoxyacetylthio)-deacetoxycephalosporanic acid, or their salts, e.g., hydrochloride salt, 22.8% by weight of starch or lactose, and 2.2% by weight of magnesium stearate. Oral suspensions might, for example, contain about 3.4% by weight of 6β-(phenylcarbothio)penicillanic acid, 5.0% by weight aluminum monostearate, 0.2% by weight of sorbitan monooleate surface active agent, and about 91.48% by weight peanut oil.

EXAMPLE 1

βββ-trichloroethyl-6-diazopenicillanate

A solution of βββ-trichloroethyl phenylacetamidopenicillanate (10.5 g, 22.6 mmol) in methylene chloride (100 ml) was added in 20 min. with stirring at −5° to a mixture of anhydrous sodium acetate (22 g), dinitrogen tetroxide (120 ml of a solution of 24 g. in 250 ml of methylene chloride) and methylene chloride (100 ml). Additional portions, 30 ml and 100 ml, of the dinitrogen tetroxide solution were added immediately and 30 minutes, respectively, after addition of the penicillin, etc., and the mixture was stirred at below 0° C for one hour. Excess dinitrogen tetroxide was consumed by contact with saturated sodium bicarbonate solution and the aqueous phase was extracted with methylene chloride. The combined organic extracts were washed with water, dried over sodium sulfate and evaporated to a yellow syrup (11 g) of crude βββ-trichloroethyl-6β-N-nitroso-phenylacetamidopenicillanate.

This ester was dissolved in methylene chloride (300 ml) and pyridine (3 ml) added. Subsequent to a 3 hour reflux, the brown solution was washed with water, saturated sodium bicarbonate, and water, dried over sodium sulfate and concentrated to a brown crystalline mass. Recrystallization from carbon tetrachloride-petroleum ether afforded the diazo compound (5.85 g 72%); mp 103.5°–104° C.

EXAMPLE 2

Phenacyl-7-diazodeacetoxycephalosporanate

In an analogous manner the 7-diazo cephalosporanate may be produced through diazotization of phenacyl-7-acetamido-deacetoxycephalosporanate.

EXAMPLE 3

βββ-trichloroethyl-6β-phenylcarbothiopenicillanate

A solution of 2.00 g (5.8 mmol) of βββ-trichloroethyl-6-diazopenicillanate in 150 ml of carbon tetrachloride was cooled to approximately 20° C, and flushed with a slow stream of helium for 0.5 hr. Thiobenzoic acid (3.84 g, 27.8 mmol) was added and the above solution irradiated with a Hanovia 450W medium pressure lamp (pyrex filter) under a slow stream of helium at 18–20° C for 8 hrs. The solution was washed with 5% aqueous sodium bicarbonate, dried and the solvent removed under reduced pressure. Silicic acid chromotography (eluent:methylene chloride) of the residual oil afforded the trans thiol ester (6α) in 4% yield as a light brown oil. Isolation of the slower moving fraction, produced the cis-thiol ester (6α) in 51% yield. This latter ester on recrystallization from ether afforded a white crystalline solid, mp 103.5–104° C IR (CHCl$_3$):3010, 2960, 1780 and 1675 cm$^{-1}$; nmr (CDCl$_3$): 1.58 (s,3H), 1.73(s,3H), 4.53 (s,1H), 4.68 (s, 2H), 5.47 (d,1H,J=4.0Hz), 5.60 (d,1H,J=4.0Hz), 7.03–8.00 (m,5H).

Anal. Calcd. for C$_{17}$H$_{16}$NO$_4$Cl$_3$S$_2$:
C, 43.56; H, 3.44; N, 2.99; Cl, 22.69; S, 13.68 .
Found:
C, 43.20; H, 3.81; N, 2.84; Cl, 22.46; S, 13.66.

EXAMPLE 4

Phenacyl-7β-(phenylcarbothio)deacetoxycephalosporanate

In a similar fashion phenacyl-7-diazodeacetoxycephalosporanate may be converted to the 7β-thiolester by irradiation in the presence of thiobenzoic acid.

EXAMPLE 5

6β-(phenylcarbothio)penicillinac acid

The 6β-thiolester prepared above was dissolved in N,N-dimethylformamide and the cooled solution combined with 90% acetic acid (5–10 mis). Stirring the acidic mixture with zinc dust (1.0–1.5 g) for 5 hrs., filtering the zinc through celite into a flask containing ice water (100 ml) and washing the zinc with methylene chloride gave a two-phase system. Separation of the organic layer and additional methylene chloride extracts yielded on drying and solvent removal (2-3 mm) a brown oil. Dissoluton of the oil in methylene chloride and extraction with 5% sodium bicarbonate, the aqueous layer being washed with methylene chloride and acidified at 0° with dilute hydrochloride acid, afforded the free acid. Extraction with methylene chloride, drying and solvent removal allowed isolation of same, which is stored at −15° C.

The minimum inhibitory concentration (MIC) in μg of active mterial per ml is <0.4 for Bacillus subtilis ATCC 6051.

EXAMPLE 6

7β-(phenylcarbothio)deacetoxycephalosporanic acid

In a similar manner the 7β-thiolcephalosporanate may be transformed to the free acid.

EXAMPLE 7

βββ-trichloroethyl-6β-(phenylacetylthio)penicillanate

A reaction sequence as above employing phenylthioacetic acid afforded the trans-thiolester in 3% yield as a light brown oil and a recrystallized (ether petroleum ether) cis-(6β)thiolester in 50% yield, mp 83–84°. IR (CHCl$_3$): 3005, 2955, 1770 and 1700 cm$^{-1}$; nmr (CDCl$_3$): 1.60 (s,3H); 1.70 (s,3H); 3.83 (s,2H); 4.54 (s,1H); (s,2H); 5.33 (d,1H,J=4.0Hz); 5.55 (d,1H,J=4.0Hz); 7.18 (s,5H).

Anal. Calcd. for C$_{18}$H$_{18}$NO$_4$Cl$_3$S$_2$:
C, 44.78; H, 3,76; N, 2.90; Cl, 22.03; S, 13.28.
Found:
C, 44.70; H, 3.60; N, 2.86; Cl, 22.0; S, 13.59.

EXAMPLE 8

6β-(phenylacetylthio)penicillanic acid

Similar zinc/acetic acid treatment of this 6β-thiolester affords the free acid in as high as 85% yield.

The MIC in μg of active material per ml is <0.4 for Bacillus subtilis ATCC 6051.

EXAMPLE 9

βββ-trichloroethyl-7β-(phenylacetylthio)deacetoxycephalosparanate

In a similar photoreaction of βββ-trichloroethyl-7-diazodeacetoxycephalosporanate and phenylthioacetic acid the 7β-thiol ester will be produced.

EXAMPLE 10

7β-(phenylacetylthio)deacetoxycephalosporanic acid

Treatment of the 7β-thiol ester with zinc/acetic acid affords the free acid.

EXAMPLE 11

βββ-trichloroethyl-6β-(benzylthio)penicillanate

A solution of 2.00 g (5.58 mmol) of βββ-trichloroethyl-6-diazopenicillanate and 3.25 ml (27.6 mmol) of benzylmercaptan in 150 ml carbon tetrachloride is flushed with a slow stream of helium for 0.5 hr. and then irradiated with a Hanovia 450W medium pressure lamp (pyrex filter) under a slow stream of helium at 38–40° C for 22 hrs. The solvent is removed under reduced pressure and the residue chromatographed on silicic acid using methylene chloride carbon tetrachloride as eluent. The faster moving fraction, a light brown oil, affords the trans-sulfide in 7% yield. The slower moving fraction, a brown solid, on recrystallization from methylene choride-pet ether yielded the cis (6β) sulfide as white needles, mp, 82–83°, in 289% yield. IR (CHCl$_3$); 1770 cm$^{-1}$; nmr (CDCl$_3$): 1.60 (s,3H), 1.70 (s,3H), 3.83 (s,2H), 4.53 (s,1H), 4.73 (s,2H), 5.33 (d,1H,J=4.0Hz), 5.55 (d,1H,J=4.0Hz), 4.18 (s,5H).

Anal. Calcd. for C$_{18}$H$_{18}$NO$_3$Cl$_3$S$_2$:
C, 44.89; 3.99; N, 3.08; Cl, 23.28; S, 14.10.
Found:
C, 44.79; H, 3.94; N, 3.08; Cl, 23.54; S, 14.30.

EXAMPLE 12

6β-(benzylthio)penicillanic acid

Similar zinc/acetic acid treatment of the sulfide affords the free acid in 91% yield.

The MIC in μg of active material per ml is 100 for Bacillus Subtillis ATCC 6051, Sarcina lutea and Shifella sonei.

EXAMPLE 13

βββ-trichloroethyl-6β-(chloroacetylthio)penicillanate

A solution of 2.00 g (5.58 mmol) of βββ-trichloroethyl-6-diazopenicillanate in 150 ml of carbon tetrachloride is cooled to approximately 3° and flushed with a slow stream of helium for 0.5 hr. To the cooled solution, chlorothioacetic acid (3.08 g, 27.9 mmol) in carbon tetrachloride (20 ml) is added dropwise over 0.5 hr. The resulting solution is irradiated with a Hanovia 450W medium pressure lamp (pyrex filter) under a slow stream of helium at 3–5° C for 15 hrs. The solution is washed with 5% aqueous sodium bicarbonate, dried, and the solvent removed under reduced pressure. Chromatography (silicic acid/methylene chloride) of the residual oil affords the trans-chloride in 3% yield, the trans thiolester in 4% yield and the cis-thiolester (6β) in 49% yield as a light brown oil. nmr (CDCl$_3$): 1.63 (s,3H); 1.73 (s,3H); 1.73 (s,3H) 4.22 (s,2H); 4.53 (s,1H); 4.73 (s,2H); 5.30 (d,1H,J=4.0Hz); 5.58 (d,1H=4.0Hz).

EXAMPLE 14

Benzhydryl-7β-(phenoxyacetylthio)deacetoxycephalosporanate

Treatment of benzhydryl-7-diazodeacetoxycephalosporanate with phenoxythioacetic acid in similar manner will afford the 7β-thiolester.

EXAMPLE 15

βββ-trichloroethyl-6β-mercaptopenicillanate

Sodium methoxide (43 mg, 0.80 mmol) in methanol (20 ml) is added dropwise over 2 hrs. to a stirred solution of 349 mg (0.79 mmol) of βββ-trichloroethyl-6β-(chloroacetylthio)phenicillanate in methanol (30 ml) at −78° C (dry ice-acetone). After the addition is complete, the stirring of the reaction mixture is continued for 5.5 hrs. at −78° C and at −50 to −65° C (dry ice-acetonitrile) for 3.5 hrs. The resulting solution is washed with ice cold 10% hydrochloric acid, dried and the solvent removed under reduced pressure without heating. The residual oil is dissolved in methylene chloride and washed with 5% sodium bicarbonate; the organic layer being dried and the solvent removed in vacuo. Chromatography (silicic acid 1:1 CH$_2$Cl$_2$—CCl$_4$) affords the mercaptan (229 mg 80%) as a yellow oil. IR (neat): 2955 and 2559 and 1774 cm$^{-1}$; nmr (CDCl$^3$): 1.67 (s,3H); 1.80 (s,3H); 2.48 (d,1H,J=21Hz); 4.40–4.73 (m,2H; H-3 and H-6); 4.79 (s,2H); and 5.60 (d,1H,J=4.0Hz).

EXAMPLE 16

Benzhydral-7β-(mercapto)deacetoxycephalosporanate

In like fashion cleavage of the phenoxyacetyl-sulfur linkage affords the mercaptoecephalosporanate.

EXAMPLE 17

βββ-trichloroethyl-6β-(phenylcarbothio)penicillanate

The above described mercaptan (98 mg, 0.27 mmol) is dissolved in ethylene chloride (5 ml) and pyridine (26 μl, 0.32 mmol) and benzoyl chloride 27 Lμl, 0.32 mmol) are added (in that order). The resulting solution is stirred at ambient temperature for 21 hrs., washed with cold 10% hydrochloric acid and 5% sodium bicarbonate, dried and the solvent removed in vacuo. Chromatography (silica gel, 2% ether in methylene chloride) of the residual oil affords a solid major fraction (112 mg, 89%). Recrystallization from ether-pet ether yields a material which is the same as obtainable through irradiation of βββ-trichloroethyl-6-diazopenicillanate and thiobenzoic acid, described in Example 3 above.

EXAMPLE 18

Benzhydral-7β-(phenoxyacetylthio)deacetoxycephalosporanate

Treatemnt of the 7β-mercapto ester with phenoxyacetylchloride will afford the same 7β-thiolester as that obtainable from the photolysis of benzhydral-7-diazodeacetoxycephalosporanate and phenoxythioxacetic acid, described in Example 14 above.

EXAMPLE 19

βββ-trichloroethyl-6β-(phenylcarbothio)penicillanate-1-oxide

To an ice cold solution of βββ-trichloroethyl-6β-(phenylcarbothio)penicillanate (1.24 g, 2.64 mmol) in chloroform (50 ml) a solution of m-chloroperbenzoic acid (454 mg, 2.63 mmol) in chloroform (20 ml) is added dropwise over 0.5 hr. Having been stirred for 2 hrs. subsequent to the addition, the resultant solution is washed with 5% sodium bicarbonate, dried and the solvent removed in vacuo. Trituration of the residual oil with either affords a crystalline material (1.04 g. 81%), and recrystallization from methylene chloride-pet ether yields the 6β-sulfoxide as white needles, mp-178°-179° C. Ir (CDCl₃): 3005, 1805, 1760 sh and 1669 cm⁻¹; nmr (CDCl₃): 1.37 (s,3H); 1.80 (s,3H); 1.80 (s,3H); 4.63 (d,1H,J=12.0Hz); 4.77 (s,1H); 5.03 (d,1H,J=12.0 Hz); 5.30 (d,1H,J=4.0Hz); 6.03 (d,1H,J=4.0Hz); 7.20-8.20 (m,5H).

Anal. Calcd. for C₁₇H₁₆NO₅Cl₃S₂:
C, 42.12; H, 3.33 N, 2.89; Cl, 21.94; S, 13.23.
Found:
C, 42.19; H, 3.26; N, 2.87; Cl, 21.97; S, 13.21.

EXAMPLE 20

βββ-trichloroethyl-7β-(phenylcarbothio)deacetoxycephalosporanate

A solution of the above sulfoxide (963 mg, 1.98 mmol) in benzene (32 ml dried over sodium wire), dimethylacetamide (24 and methanesulfonic acid (3 drops) was azeotropically refluxed, using a Dean-Stark strap, for 19 hrs. in a bath maintained at 110-120°. Following the reflux, the solvent was removed in vacuo and the dark brown residue chromatographically separated (silicic acid-methylene chloride) to afford the thiol ester (659 mg, 71% as a white solid. Recrystallization from methylene chloride-pet ether gave an analytically pure sample, mp 175.5°-176.0° C. Ir (CHCl₃): 3005, 1780, 1740 sh and 1670 cm⁻¹; nmr (CDCl₃): 2.23 (s,3H); 3.33 (d,2H,J=5.0Hz); 4.70 (d,1H,J=13.0Hz); 5.03 (d,1H,J=13.0Hz); 5.10 (d,1H,J=4.0Hz); 5.64 (c,1H,J4.0Hz); 7.10-8.20 (m,5H).

Anal. Calcd. for C₁₇H₁₄NO₄Cl₃S₂:
C,43.74; H, 3.02; N, 3.00; Cl, 22.78; S, 13.74.
Found: C, 43.66; H, 3.04; N, 3.01; Cl, 22.73; S, 13.64.

EXAMPLE 21

7β-(phenylcarbothio)deacetoxycephalosporanic acid

The above thiolester was dissolved in N,N-dimethylformaide and to this cooled solution 5-10 ml of 90% acetic acid was added. Zinc dust (1.0-1.5 g) having been added, the reaction mixture was stirred for 5 hrs. at 0° C. Removal of the zinc through celite into a filtration flask containing ice water (100 ml) and washing of the zinc with methylene chloride yielded a two-phase system. Separation of the organic layer, extraction of the aqueous layer with several additional methylene chloridezinc washings, combination of all the organic layers, drying and removal of solvent in vacuo (2-3 mm) afforded a residual oil. This oil was dissolved in methylene chloride and extracted with 5% sodium bicarbonate. The aqueous layer, after being washed with methylene chloride, was cooled and acidified with dilute hydrochloric acid. Extraction of the acidic solution with methylene chloride and drying this organic extract gave the free acid on removal of solvent. The acid is stored at −15° C prior to bioassay. MIC:Staphylococcus fecalis (50), bacillus subtilis ATCC 6051 (25), aerobacter aerogenes (100), and proteus mirabilis (50). This same acid may be prepared from phenacyl-7β-)phenylcarbothio)deacetoxycephalosporanate, as described in Example 6 above.

EXAMPLE 22

Phenyl-7β-(phenylcarbothio)deacetoxycephalosporanate

The above thiol aci on esterification with phenacylchloride will afford the same phenacyl thiol ester as that which may be obtained on the irradiation of phenacyl-7-diazodeacetoxycephalosporanate, as described in Example 4 above.

EXAMPLE 23

βββ-trichloroethyl-7β-(phenylacetylthio)deacetoxycephalosporanate

In the same manner described above, βββ-trichloroethyl-6β-(chloroacetylthio)pencillinate was transformed to the 7β-thiol ester, mp 102-104.5; Ir (CHCl₃): 3005, 1780, and 1730 cm⁻¹; nmr (CDCl₃): 1.85 (s,3H); 3.28 (d,2H,J=6.0Hz); 3.67 (s,2H); 6.33 (d,1H,J=12.0Hz); 4.95 (d,1H,J=12.0Hz); 4.95 (d,1H,J=4.0Hz); 5.33 (d,1H,J=4.0Hz); 7.10 (s,3,H).

Anal. Calcd. for C₁₈H₁₆NO₄CL₃S₂;
C, 44.96; H, 3.35; N, 2.91; Cl, 22.12; S, 13.34.
Found:
C, 44.97; H, 3.38; N, 2.84; Cl, 22.10; S, 13.16. This is the same compound which may be prepared by irradiation as described in Example 9,. above.

EXAMPLE 24

βββ-trichloroethyl-7β-(mercapto)deacetoxycephalosporanate

To a stirred methanolic solution of this thiol ester (369 mg, 9.03 mmol), at −78° C (dry ice-acetone) sodium methoxide (49 mg, 9.08 mmol) in methanol (25 ml) is added dropwise over 2 hrs. Following the addition, the reaction mixture is stirred at −78° C for 5.5 hrs. and at −50° to −65° C (dry ice-acetonitril) for 3.5 hrs. The solution is washed in cold 10% hydrochloric acid, dried and the solvent removed in vacuo without heating. The residue was dissolved in methylene chloride and washed with 5% sodium bicarbonate. The organic layer, after having been dried and the solvent removed in vacuo, afforded a brown oil. Chromatographic purification (silicic acid, methylene chloridecarbon tetrachloride) permitted isolation of the mercaptan in 75% yield. nmr (CDCl₃): 2.32 (d,4H,J=4.0Hz, CH₃ and −SH); 3.38 (d,2H,J=4.0Hz) 4.50-5.00 (m,3H, CH₂CCl₃ and C₆); 5.01 (d,1H, J=4.0Hz).

EXAMPLE 25

7β-(phenoxyacetylthio)deacetoxycephalosporanic acid

The mercaptum was dissolved in methylene chloride (5 ml) and pyridine and phenoxyacetylchloride were added sequentially. The resulting solution was stirred at ambient temperature for 20 hrs. washed with 10% hydrochloric acid and 5% sodium bicarbonate, dried, and the solvent removed under reduced pressure. Chromatography of the residual oil (silica gel, 2% ether-methylene chloride) afforded as the major fraction the thiol ester. Removal of the βββ-trichloro protective group in the standard fashion gave the free acid. This acid is the same as that which can be isolated from benzhydryl-7β-(phenoxyacetylthio)deacetoxycephalosporanate.

EXAMPLE 26

7β-(phenylacetylthio)deacetoxycephalosporanic acid

Treatment of the 7β-mercaptan with phenylacetyl chloride produces 7β-(phenacetylthio)deacetoxycephalosporanic acid. Such acid displays the following MIC in μg per ml: staphylococcus aureus 100 (100), bacillus subtilis ATCC 6051 (100).

The embodiments of the invention which have been described and illustrated is intended to be exemplary only, and many modifications will be apparent to those

We claim:
1. A compound having the formula:

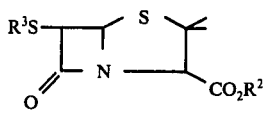

wherein $R^2$ is a conventional penicillin pharmaceutically acceptable group and $R^3$ is hydrogen or an organic moiety which is electrophyllic as compared to the sulfur to which it is attached, selected from the group of lower alkyl cyclopentyl, cyclohexyl, methycyclohexyl, phenyl, benzyl, tolyl, and a conventional pencillin side chain acyl radicals.

2. The compound of claim 1 wherein $R^2$ is selected from the group of hydrogen, substituted and unsubstituted aliphatic, alicyclic, aromatic, acyl and organosilyl radicals, alkali metal ions and quaternary ammonium ions.

3. The compound of claim 1 wherein $R^2$ is selected from the group of alkyl, alkenyl, alkinyl, cycloalkyl, cycloalkenyl, aryl, aralkyl, alkaryl, acyl, acylamino, acylaminoalkyl, imino and acrylacyl.

4. The compound of claim 1 wherein $R^2$ is $\beta\beta\beta$-trichloroethyl.

5. The compound of claim 1 wherein $R^2$ is benzyl.

6. The compound of claim 1 wherein $R^2$ is benzhydral.

7. The compound of claim 1 wherein $R^2$ is hydrogen.

8. The compound of claim 1 wherein $R^2$ is selected from the group of sodium and potassium.

9. The compound of claim 1 wherein $R^2$ is t-butyl.

10. The compound of claim 2 wherein $R^2$ is trialkylsilyl.

11. The compound of claim 1 wherein $R^3$ is a conventional penicillin, sidechain acyl radical.

12. The compound of claim 1 wherein $R^3$ is selected from the group of hydrogen, formyl, acetyl, phenyl, phenylacetyl, phenoxyacetyl, p-aminophenylacetyl, $\alpha$-carboxylphenylacetyl, benzyl, benzoyl, 2-thienylacetyl, aminocarbamyl, phenylglycyl, methyl sulfonyl, benzyl sulfonyl, o-aminophenylsulfonyl, p-aminobenzylsulfonly, carbobenzoxy, $\alpha$-carbonaphthoxy, carbo(2-thienylmethoxy), and (1-phenyl,2-formylamino)ethoxycarbonyl.

13. The compound of claim 11 wherein $R^3$ is hydrogen.

14. The compound of claim 11 wherein $R^3$ is benzoyl.

15. The compound of claim 11 wherein $R^3$ is phenylacetyl.

16. The compound of claim 11 wherein $R^3$ is benzyl.

17. The compound of claim 11 wherein $R^3$ is chloroacetyl.

18. The compound of claim 11 wherein $R^3$ is phenoxyacetyl.